US006187571B1

(12) United States Patent
Pignard et al.

(10) Patent No.: US 6,187,571 B1
(45) Date of Patent: Feb. 13, 2001

(54) USE OF A DNA SEQUENCE CODING FOR A PROTEIN CAPABLE OF DEGRADING OXALIC ACID AS SELECTION GENE

(75) Inventors: Annie Pignard, Roquettes; Bruno Grezes-Besset, Colomiers; René Grison, Escalquens; Michel Schneider, Toulouse, all of (FR)

(73) Assignee: Biogemma, Paris (FR)

( * ) Notice: Under 35 U.S.C. 154(b), the term of this patent shall be extended for 0 days.

(21) Appl. No.: 08/448,398

(22) PCT Filed: Dec. 7, 1993

(86) PCT No.: PCT/FR93/01203

§ 371 Date: Oct. 24, 1995

§ 102(e) Date: Oct. 24, 1995

(87) PCT Pub. No.: WO94/13790

PCT Pub. Date: Jun. 23, 1994

(30) Foreign Application Priority Data

Dec. 7, 1992 (FR) .................................................. 92 14721

(51) Int. Cl.[7] ........................... C12N 15/09; C12N 15/29; C12N 5/10
(52) U.S. Cl. ...................... 435/172.3; 435/69.1; 800/278; 800/279; 536/23.2; 536/23.6

(58) Field of Search ................................. 435/172.3, 69.1, 435/412, 414, 416, 418; 536/23.2, 23.6; 800/205, DIG. 43, DIG. 17, DIG. 14, 279, 278, 298, 301; 47/58

(56) References Cited

PUBLICATIONS

Lewin. When does homology mean something else? Science. vol. 237, p. 1570, 1987.*
Dumas et al. Tissue–specific expression of germin–like oxalate oxidase during development and fungal infection of barley seedlings. Plant Physiol. 107:1091–1096, 1995.*
Zhang et al. Germin–like oxalate oxidase, a $H_2O_2$–producing enzyme, accumulates in barley attacked by the powdery mildew funguss. Plant Journal 8:139–145, 1995.*

* cited by examiner

*Primary Examiner*—Paula K. Hutzell
*Assistant Examiner*—Melissa L. Kimball
(74) *Attorney, Agent, or Firm*—Dennison, Scheiner, Schultz & Wakeman

(57) ABSTRACT

The invention relates to the novel use of a sequence coding for a protein capable of degrading oxalic acid to select plant cells which have integrated a gene of interest, and a novel process for selecting, on oxalic acid, cells, calluses or plants transformed by this recombinant DNA.

8 Claims, No Drawings

SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
      (A) LENGTH: 224 amino acids
      (B) TYPE: amino acid
      (D) TOPOLOGY: linear (ii) MOLECULE TYPE: protein (xi) SEQUENCE DESCRIPTION: SEQ ID NO: 1:

```
Met Gly Tyr Ser Lys Thr Leu Val Ala Gly Leu Phe Ala Met Leu Leu
1               5                   10                  15

Leu Ala Pro Ala Val Leu Ala Thr Asp Pro Asp Pro Leu Gln Asp Phe
                20                  25                  30

Cys Val Ala Asp Leu Asp Gly Lys Ala Val Ser Val Asn Gly His Thr
            35                  40                  45

Cys Lys Pro Met Ser Glu Ala Gly Asp Asp Phe Leu Phe Ser Ser Lys
        50                  55                  60

Leu Ala Lys Ala Gly Asn Thr Ser Thr Pro Asn Gly Ser Ala Val Thr
65                  70                  75                  80
```

```
Glu Leu Asp Val Ala Glu Trp Pro Gly Thr Asn Thr Leu Gly Val Ser
                85                  90                  95

Met Asn Arg Val Asp Phe Ala Pro Gly Gly Thr Asn Pro Pro His Ile
                100                 105                 110

His Pro Arg Ala Thr Glu Ile Gly Ile Val Met Lys Gly Glu Leu Leu
                115                 120                 125

Val Gly Ile Leu Gly Ser Leu Asp Ser Gly Asn Lys Leu Tyr Ser Arg
                130                 135                 140

Val Val Arg Ala Gly Glu Thr Phe Leu Ile Pro Arg Gly Leu Met His
145                 150                 155                 160

Phe Gln Phe Asn Val Gly Lys Thr Glu Ala Ser Met Val Val Ser Phe
                165                 170                 175

Asn Ser Gln Asn Pro Gly Ile Val Phe Val Pro Leu Thr Leu Phe Gly
                180                 185                 190

Ser Asn Pro Pro Ile Pro Thr Pro Val Leu Thr Lys Ala Leu Arg Val
                195                 200                 205

Glu Ala Arg Val Val Glu Leu Leu Lys Ser Lys Phe Ala Ala Gly Phe
                210                 215                 220
```

(2) INFORMATION FOR SEQ ID NO: 2:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
ATGGGGTACT CCAAAACCCT AGTAGCTGGC GTGTTCGCAA TGCTGTTACT AGCTCCGGCC     60
GTCTTGGCCA CCGACCCAGA CCCTCTCCAG GACTTCTGTG TCGCCGACCT CGACGGCAAG    120
GCGGTCTCGG TGAACGGGCA CACGTGCAAG CCCATGTCGG AGGCCGGCGA CGACTTCCTC    180
TTCTCGTCCA AGTTGGCCAA GGCCGGCAAC ACGTCCACCC CGAACGGCTC CGCCGTGACG    240
GAGCTCGACG TGGCCGAGTG GCCCGGTACC AACACGCTGG GTGTGTCCAT GAACCGCGTG    300
GACTTTGCTC CCGGAGGCAC CAACCCACCA CACATCCACC CGCGTGCCAC CGAGATCGGC    360
ATCGTGATGA AGGTGAGCT TCTCGTGGGA ATCCTTGGCA GCCTCGACTC CGGGAACAAG    420
CTCTACTCGA GGGTGGTGCG CGCCGGAGAG ACGTTCCTCA TCCCACGGGG CCTCATGCAC    480
TTCCAGTTCA ACGTCGGTAA GACCGAGGCC TCCATGGTCG TCTCCTTCAA CAGCCAGAAC    540
CCCGGCATTG TCTTCGTGCC CCTCACGCTC TTCGGCTCCA ACCCGCCCAT CCCAACGCCG    600
GTGCTCACCA AGGCACTCCG GGTGGAGGCC AGGGTCGTGG AACTTCTCAA GTCCAAGTTT    660
GCCGCTGGGT TT                                                        672
```

(2) INFORMATION FOR SEQ ID NO: 3:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO: 3:

```
Gly Gly Asp Leu Gly Ser Val Ile Ser Asn Ser Met Phe Asp Gln Met
1               5                   10                  15
```

-continued

```
Leu Lys His Arg Asn Glu Asn Ser Cys Gln Gly Lys Asn Asn Phe Tyr
             20                  25                  30

Ser Tyr Asn Ala Phe Ile Thr Ala Ala Arg Ser Phe Pro Gly Phe Gly
             35                  40                  45

Thr Ser Gly Asp Ile Asn Ala Arg Lys Arg Glu Ile Ala Ala Phe Phe
 50                  55                  60

Ala Gln Thr Ser His Glu Thr Thr Gly Gly Trp Pro Ser Ala Pro Asp
 65                  70                  75                  80

Gly Pro Phe Ala Trp Gly Tyr Cys Phe Leu Arg Glu Arg Gly Asn Pro
                 85                  90                  95

Gly Asp Tyr Cys Ser Pro Ser Ser Gln Trp Pro Cys Ala Pro Gly Arg
                100                 105                 110

Lys Tyr Phe Gly Arg Gly Pro Ile Gln Ile Ser His Asn Tyr Asn Tyr
                115                 120                 125

Gly Pro Cys Gly Arg Ala Ile Gly Val Asp Leu Leu Asn Asn Pro Asp
                130                 135                 140

Leu Val Ala Thr Asp Pro Val Ile Ser Phe Lys Thr Ala Ile Trp Phe
145                 150                 155                 160

Trp Met Thr Pro Gln Ser Pro Lys Pro Ser Cys His Asp Val Ile Ile
                165                 170                 175

Gly Arg Trp Asn Pro Ser Ala Gly Asp Arg Ser Ala Asn Arg Leu Pro
                180                 185                 190

Gly Phe Gly Val Ile Thr Asn Ile Ile Asn Gly Gly Leu Glu Cys Gly
                195                 200                 205

Arg Gly Asn Asp Asn Arg Val Gln Asp Arg Ile Gly Phe Tyr Arg Arg
                210                 215                 220

Tyr Cys Gly Ile Leu Gly Val Ser Pro Gly Asp Asn Leu Asp Cys Gly
225                 230                 235                 240

Asn Gln Arg Ser Phe Gly Asn Gly Leu Leu Val Asp Thr Met
                245                 250
```

(2) INFORMATION FOR SEQ ID NO: 4:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO: 4:

```
Met Arg Arg Thr Ser Lys Leu Thr Thr Phe Ser Leu Leu Phe Ser Leu
 1               5                  10                  15

Val Leu Leu Ser Ala Ala Leu Ala
             20
```

(2) INFORMATION FOR SEQ ID NO: 5:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO: 5:

```
Gln Asn Cys Gly Ser Gln Gly Gly Gly Lys Val Cys Ala Ser Gly Gln
 1               5                  10                  15

Cys Cys Ser Lys Phe Gly Trp Cys Gly Asn Thr Asn Asp His Cys Gly
```

```
              20                  25                  30
Ser Gly Asn Cys Gln Ser Gln Cys Pro Gly Gly Gly Pro Gly
         35                  40                  45
Pro Val Thr
  50
```

(2) INFORMATION FOR SEQ ID NO: 6:

(i) SEQUENCE CHARACTERISTICS:
        (A) LENGTH: 1153 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION:443..521

(ix) FEATURE:
        (A) NAME/KEY: intron
        (B) LOCATION:676..756

(xi) SEQUENCE DESCRIPTION: SEQ ID NO: 6:

```
ATGAGGCGAA CTTCTAAATT GACTACTTTT TCTTTGCTGT TTTCTCTGGT TTTGCTGAGT     60
GCTGCCTTGG CACAGAATTG TGGTTCACAG GGCGGAGGCA AGTTTGTGC GTCGGGACAA    120
TGTTGCAGCA AATTCGGGTG GTGCGGTAAC ACTAATGACC ATTGTGGTTC TGGCAATTGT    180
CAAAGTCAGT GTCCAGGTGG CGGCCCTGGT CCTGGTCCTG TTACTGGTGG GGACCTCGGA    240
AGCGTCATCT CAAATTCTAT GTTTGATCAA ATGCTTAAGC ATCGTAACGA AAATTCTTGT    300
CAAGGAAAGA ATAATTTCTA CAGTTACAAT GCCTTTATTA CTGCTGCTAG GTCTTTTCCT    360
GGCTTTGGTA CAAGTGGTGA TATCAATGCC CGTAAAAGGG AAATTGCTGC TTTCTTTGCC    420
CAAACCTCCC ATGAAACTAC TGGTATGTGT ATAACCATTC ACATCGAACC ATTAAAATAT    480
AATTTCATTT TATTTTATTT AGTAATTGAT TATATATGTA GGAGGATGGC CTTCCGCACC    540
TGATGGACCA TTCGCATGGG GTTACTGTTT CCTTAGAGAA CGAGGTAACC CCGGTGACTA    600
CTGTTCACCA AGTAGTCAAT GGCCTTGTGC ACCTGGAAGG AAATATTTCG ACGAGGCCCC    660
AATCCAAATT TCACAGTAAG CTACATAAAT CTATATATGG TAAAATTTGA TGAACTTGTA    720
GTGTCTAATT ACGTGTATTT TGACATTTCA AAACAGCAAC TACAACTATG GGCCATGTGG    780
AAGAGCCATC GGAGTGGACC TTTTAAACAA TCCTGATTTA GTAGCCACAG ACCCAGTCAT    840
CTCATTCAAG ACTGCTATCT GGTTCTGGAT GACCCCTCAA TCACCAAAGC CTTCTTGCCA    900
CGATGTCATC ATTGGAAGAT GGAACCCATC TGCCGGTGAC CGATCAGCCA ATCGTCTTCC    960
TGGATTTGGT GTCATCACAA ACATCATCAA TGGGGGCCTG GAATGTGGTC GTGGCAATGA   1020
CAATAGGGTC CAGGATCGCA TTGGGTTTTA CAGGAGGTAT TGCGGTATTC TTGGTGTTAG   1080
TCCTGGTGAC AATCTTGATT GCGGAAACCA GAGATCTTTT GGAAACGGAC TTTTAGTCGA   1140
TACTATGTAA TGA                                                     1153
```

(2) INFORMATION FOR SEQ ID NO: 7:

(i) SEQUENCE CHARACTERISTICS:
        (A) LENGTH: 389 amino acids
        (B) TYPE: amino acid
        (D) TOPOLOGY: linear (ii) MOLECULE TYPE: protein (xi) SEQUENCE DESCRIPTION: SEQ ID NO: 7:

```
Gly Ser Gly Phe Ala Asn Ala Val Tyr Phe Thr Asn Trp Gly Ile Tyr
1               5                   10                  15

Gly Arg Asn Phe Gln Pro Ala Asp Leu Pro Ala Ser Glu Ile Thr His
            20                  25                  30

Val Leu Tyr Ser Phe Met Asn Val Arg Ala Asp Gly Thr Ile Phe Ser
        35                  40                  45

Gly Asp Thr Tyr Ala Asp Tyr Glu Lys His Tyr Ala Gly Asp Ser Trp
    50                  55                  60

Asn Asp Val Gly Thr Asn Ala Tyr Gly Cys Val Lys Gln Leu Tyr Leu
65                  70                  75                  80

Leu Lys Lys Gln Asn Arg Asn Met Lys Val Met Leu Ser Ile Gly Gly
                85                  90                  95

Trp Thr Trp Ser Thr Asn Phe Pro Ala Ala Ser Ser Ala Ala Thr
            100                 105                 110

Arg Lys Thr Phe Ala Gln Ser Ala Val Gly Phe Met Lys Asp Trp Gly
            115                 120                 125

Phe Asp Gly Ile Asp Ile Asp Trp Glu Tyr Pro Ala Asp Ala Thr Gln
130                 135                 140

Ala Gln Asn Met Val Leu Leu Leu Gln Ala Val Arg Ser Glu Leu Asp
145                 150                 155                 160

Ser Tyr Ala Ala Gln Tyr Ala Lys Gly His His Phe Leu Leu Ser Ile
                165                 170                 175

Ala Ala Pro Ala Gly Pro Asp Asn Tyr Asn Lys Leu Lys Phe Ala Glu
                180                 185                 190

Leu Gly Lys Val Leu Asp Tyr Ile Asn Leu Met Ala Tyr Asp Tyr Ala
                195                 200                 205

Gly Ser Trp Ser Asn Tyr Thr Gly His Asp Ala Asn Ile Tyr Ala Asn
    210                 215                 220

Pro Gln Asn Pro Asn Ala Thr Pro Tyr Asn Thr Asp Asp Ala Val Gln
225                 230                 235                 240

Ala Tyr Ile Asn Gly Gly Val Pro Ala Asn Lys Ile Val Leu Gly Met
                245                 250                 255

Pro Ile Tyr Gly Arg Ser Phe Gln Gln Thr Glu Gly Ile Gly Lys Pro
                260                 265                 270

Tyr Asn Gly Ile Gly Ser Gly Ser Trp Glu Asn Gly Ile Trp Asp Tyr
            275                 280                 285

Lys Ala Leu Pro Lys Ala Gly Ala Thr Val Lys Cys Asp Asp Thr Ala
            290                 295                 300

Lys Gly Cys Tyr Ser Tyr Asp Pro Ser Thr Lys Glu Leu Ile Ser Phe
305                 310                 315                 320

Asp Thr Pro Ala Met Ile Ser Thr Lys Val Ser Trp Leu Lys Gly Lys
                325                 330                 335

Gly Leu Gly Gly Ser Met Phe Trp Glu Ala Ser Ala Asp Lys Lys Gly
            340                 345                 350

Ser Asp Ser Leu Ile Ser Thr Ser His Gln Gly Leu Gly Ser Gln Asp
            355                 360                 365

Ser Thr Gln Asn Tyr Leu Asp Tyr Pro Asn Ser Lys Tyr Asp Asn Ile
    370                 375                 380

Lys Lys Gly Met Asn
385
```

(2) INFORMATION FOR SEQ ID NO: 8:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (vii) IMMEDIATE SOURCE:
    (B) CLONE: signal peptide (xi) SEQUENCE DESCRIPTION: SEQ ID NO: 8:

```
Met Leu Ser Phe Val Lys Lys Ser Ile Ala Leu Val Ala Ala Leu Gln
1               5                   10                  15

Ala Val Thr Ala Leu Ala
            20
```

(2) INFORMATION FOR SEQ ID NO: 9:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 9:

```
Thr Pro Ile Ser Ser Glu Ala Gly Val Glu Lys Arg
1               5                   10
```

(2) INFORMATION FOR SEQ ID NO: 10:

(i) SEQUENCE CHARACTERISTICS:
        (A) LENGTH: 1167 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
GGTAGTGGTT TTGCAAATGC CGTCTACTTC ACCAACTGGG GCATTTATGG CCGCAACTTC      60

CAGCCTGCCG ACCTTCCTGC CTCGGAGATT ACTCACGTAC TCTACTCCTT CATGAATGTC     120

CGCGCAGATG GCACCATCTT TTCCGGTGAT ACCTATGCCG ACTACGAGAA GCACTACGCT     180

GGTGACTCTT GGAACGATGT GGGCACGAAC GCTTACGGTT GTGTTAAGCA ACTTTATCTT     240

CTCAAGAAGC AGAACCGCAA CATGAAGGTG ATGCTGTCGA TTGGTGGTTG GACATGGTCT     300

ACCAACTTCC CCGCTGCCGC CAGCTCGGCT GCTACCCGAA AGACTTTTGC TCAGTCTGCT     360

GTTGGCTTCA TGAAGGACTG GGGTTTCGAC GGTATTGATA TCGACTGGGA GTACCCCGCC     420

GATGCCACTC AGGCTCAGAA TATGGTTCTC TTGCTACAGG CTGTCCGCAG TGAGCTCGAC     480

TCCTACGCTG CCCAGTACGC CAAGGGTCAC CACTTCCTGC TTTCAATTGC CGCCCCTGCT     540

GGACCTGACA ATTATAACAA GCTGAAGTTT GCTGAGCTTG GCAAGGTTCT CGATTACATT     600

AACCTCATGG CTTACGATTA CGCTGGATCT TGGAGCAACT ACACTGGCCA CGATGCCAAC     660

ATATACGCAA ACCCGCAGAA CCCCAACGCC ACCCCTTACA ACACGGACGA TGCTGTCCAG     720

GCCTATATCA ACGGCGGCGT CCCTGCCAAC AAGATCGTCC TTGGTATGCC AATCTACGGC     780

CGATCCTTCC AGCAAACCGA GGGTATCGGT AAGCCTTACA ATGGTATTGG CTCTGGTAGC     840

TGGGAGAACG GTATCTGGGA CTACAAGGCT CTCCCCAAGG CTGGTGCCAC CGTCAAGTGC     900

GACGATACCG CCAAGGGATG CTACAGCTAC GATCCAAGCA CTAAGGAGCT TATTTCTTTC     960
```

```
GATACGCCGG CTATGATCAG CACCAAAGTT AGCTGGCTCA AGGGCAAGGG CCTTGGCGGC    1020

AGCATGTTCT GGGAGGCTTC TGCCGACAAG AAGGGCTCGG ACTCTCTTAT TAGCACCAGC    1080

CACCAAGGTC TCGGTAGCCA GGACAGCACT CAGAACTACC TCGACTACCC TAACTCCAAG    1140

TACGACAACA TCAAGAAGGG CATGAAC                                        1167
```

(2) INFORMATION FOR SEQ ID NO: 11:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO: 11:

```
Ile Gly Val Cys Tyr Gly Met Leu Gly Asn Asn Leu Pro Ser Ala Asn
1               5                   10                  15

Asp Val Ile Gly Leu Tyr Arg Ser Asn Asn Ile Lys Arg Met Arg Leu
            20                  25                  30

Tyr Asp Pro Asn Gln Ala Ala Leu Glu Ala Leu Arg Asn Ser Gly Ile
        35                  40                  45

Glu Leu Ile Leu Gly Val Pro Asn Ser Asp Leu Gln Gly Leu Ala Thr
50                  55                  60

Asn Pro Asp Thr Ser Arg Gln Trp Val Gln Lys Asn Val Leu Asn Phe
65                  70                  75                  80

Trp Pro Ser Val Lys Ile Lys Tyr Val Ala Val Gly Asn Glu Val Ser
                85                  90                  95

Pro Val Gly Gly Ser Ser Val Ala Gln Tyr Val Leu Pro Ala Ile
            100                 105                 110

Gln Asn Val Tyr Gln Ala Ile Arg Ala Gln Gly Leu His Asp Gln Ile
        115                 120                 125

Lys Val Ser Thr Ser Ile Asp Met Thr Leu Ile Gly Asn Ser Phe Pro
130                 135                 140

Pro Ser Gln Gly Ser Phe Arg Gly Asp Val Arg Ser Tyr Leu Asp Pro
145                 150                 155                 160

Ile Ile Gly Tyr Leu Val Tyr Ala Asn Ala Pro Leu Leu Val Asn Val
                165                 170                 175

Tyr Pro Tyr Phe Ser Tyr Thr Gly Asn Pro Arg Asp Ile Ser Leu Pro
            180                 185                 190

Tyr Ala Leu Phe Thr Ala Pro Asn Val Val Trp Asp Gly Gln Tyr
        195                 200                 205

Gly Tyr Gln Asn Leu Phe Asp Ala Met Leu Asp Ser Val His Ala Ala
    210                 215                 220

Ile Asp Asn Thr Lys Ile Gly Tyr Val Glu Val Val Ser Glu Ser
225                 230                 235                 240

Gly Trp Pro Ser Asp Gly Gly Phe Ala Ala Thr Tyr Asp Asn Ala Arg
                245                 250                 255

Val Tyr Leu Asp Asn Leu Val Arg Ala Asn Arg Gly Ser Pro Arg
            260                 265                 270

Arg Pro Ser Lys Pro Thr Glu Thr Tyr Ile Phe Ala Met Phe Asp Glu
        275                 280                 285

Asn Gln Lys Asn Pro Glu Ile Glu Lys His Phe Gly Leu Phe Asn Pro
    290                 295                 300

Asn Lys Gln Lys Lys
305
```

(2) INFORMATION FOR SEQ ID NO: 12:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO: 12:

```
Tyr Pro Phe Gly Phe Gly Gly Lys Arg Leu Gly Lys Val Val Ile Asp
 1               5                  10                  15
Asp Phe Asn Ala Thr Thr Ser Ile Lys Ser Asp Val
                20                  25
```

(2) INFORMATION FOR SEQ ID NO: 13:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO: 13:

```
Gln Ile Gly Val Cys Tyr Gly Met Leu Gly Asn Asn Leu Pro Ser Ala
 1               5                  10                  15
Asn Asp Val Ile Gly Leu Tyr Arg Ser Asn Asn Ile Lys Arg Met Arg
                20                  25                  30
Leu Tyr Asp Pro Asn Gln Ala Ala Leu Glu Ala Leu Arg Asn Ser Gly
                35                  40                  45
Ile Glu Leu Ile Leu Gly Val Pro Asn Ser Asp Leu Gln Gly Leu Ala
 50                  55                  60
Thr Asn Pro Asp Thr Ser Arg Gln Trp Val Gln Lys Asn Val Leu Asn
 65                  70                  75                  80
Phe Trp Pro Ser Val Lys Ile Lys Tyr Val Ala Val Gly Asn Glu Val
                85                  90                  95
Ser Pro Val Gly Gly Ser Ser Ser Val Ala Gln Tyr Val Leu Pro Ala
                100                 105                 110
Ile Gln Asn Val Tyr Gln Ala Ile Arg Ala Gln Gly Leu His Asp Gln
                115                 120                 125
Ile Lys Val Ser Thr Ser Ile Asp Met Thr Leu Ile Gly Asn Ser Phe
    130                 135                 140
Pro Pro Ser Gln Gly Ser Phe Arg Gly Asp Val Arg Ser Tyr Leu Asp
145                 150                 155                 160
Pro Ile Ile Gly Tyr Leu Val Tyr Ala Asn Ala Pro Leu Leu Val Asn
                165                 170                 175
Val Tyr Pro Tyr Phe Ser Tyr Thr Gly Asn Pro Arg Asp Ile Ser Leu
                180                 185                 190
Pro Tyr Ala Leu Phe Thr Ala Pro Asn Val Val Trp Asp Gly Gln
                195                 200                 205
Tyr Gly Tyr Gln Asn Leu Phe Asp Ala Met Leu Asp Ser Val His Ala
    210                 215                 220
Ala Ile Asp Asn Thr Lys Ile Gly Tyr Val Glu Val Val Ser Glu
225                 230                 235                 240
Ser Gly Trp Pro Ser Asp Gly Gly Phe Ala Ala Thr Tyr Asp Asn Ala
                245                 250                 255
```

Arg Val Tyr Leu Asp Asn Leu Val Arg Arg Ala Asn Arg Gly Ser Pro
              260                 265                 270

Arg Arg Pro Ser Lys Pro Thr Glu Thr Tyr Ile Phe Ala Met Phe Asp
          275                 280                 285

Glu Asn Gln Lys Asn Pro Glu Ile Glu Lys His Phe Gly Leu Phe Asn
      290                 295                 300

Pro Asn Lys Gln Lys Lys Tyr Pro Phe Gly Phe Gly Gly Lys Arg Leu
305                 310                 315                 320

Gly Lys Val Val Ile Asp Asp Phe Asn Ala Thr Thr Ser Ile Lys Ser
              325                 330                 335

Asp Val (2) INFORMATION FOR SEQ ID NO: 14:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO: 14:

Met Pro Ser Leu Phe Ala Arg Asn Gln Arg Phe Ser Leu Ala Thr Leu
1               5                   10                  15

Leu Leu Leu Leu Glu Leu Leu Thr Gly Asn Leu Arg Met Ala Asp Ala
              20                  25                  30

(2) INFORMATION FOR SEQ ID NO: 15:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
ATTGGTGTGT GTTATGGCAT GCTGGGCAAC AATCTACCGT CAGCAAACGA TGTTATAGGT      60
CTTTATAGAT CAAATAACAT AAAGAGAATG AGACTCTATG ATCCTAATCA AGCTGCTCTA     120
GAAGCACTTA GAAATTCTGG CATTGAACTC ATTCTTGGGG TGCCAAACTC TGACCTTCAA     180
GGCCTTGCCA CCAATCCTGA CACTTCTCGT CAATGGGTGC AAAAAAACGT GTTGAACTTT     240
TGGCCTAGTG TCAAAATCAA GTACGTGGCA GTTGGAAATG AAGTGAGTCC CGTTGGAGGC     300
TCTTCTTCGG TAGCCCAATA TGTTCTACCT GCCATCCAAA ATGTATACCA AGCAATAAGA     360
GCTCAAGGCC TTCATGATCA AATCAAGGTT TCAACATCTA TTGACATGAC CCTAATAGGA     420
AACTCTTTCC CTCCATCGCA AGGTTCCTTC AGGGGTGATG TGAGATCATA CCTAGATCCC     480
ATAATTGGGT ACTTGGTATA TGCAAATGCA CCATTACTAG TCAATGTGTA CCCTTATTTT     540
AGTTACACTG GTAACCCCCG TGACATATCA CTTCCCTATG CTCTTTTCAC AGCACCAAAT     600
GTTGTGGTAT GGGATGGTCA ATATGGGTAC CAAAATTTGT TTGATGCTAT GTTGGATTCA     660
GTACATGCAG CCATTGATAA CACTAAGATT GGTTATGTGG AGGTTGTTGT ATCCGAGAGT     720
GGGTGGCCAT CAGATGGAGG ATTTGCTGCC ACTTATGACA ACGCACGCGT GTACTTAGAC     780
AATTTGGTTC GTCGTGCTAA TAGAGGAAGC CCAAGAAGGC CTTCGAAGCC CACTGAGACT     840
TATATATTTG CCATGTTCGA TGAAAATCAA AAAAATCCAG AGATAGAGAA ACATTTTGGG     900
CTCTTCAATC CCAACAAACA AAAAAAA                                        927
```

(2) INFORMATION FOR SEQ ID NO: 16:

(i) SEQUENCE CHARACTERISTICS:
        (A) LENGTH: 751 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION:21..692

(xi) SEQUENCE DESCRIPTION: SEQ ID NO: 16:

```
AAGCTTATTA CATAGCAAGC ATG GGG TAC TCC AAA ACC CTA GTA GCT GGC           50
                     Met Gly Tyr Ser Lys Thr Leu Val Ala Gly
                      1               5                  10

GTG TTC GCA ATG CTG TTA CTA GCT CCG GCC GTC TTG GCC ACC GAC CCA         98
Val Phe Ala Met Leu Leu Leu Ala Pro Ala Val Leu Ala Thr Asp Pro
                 15                  20                  25

GAC CCT CTC CAG GAC TTC TGT GTC GCC GAC CTC GAC GGC AAG GCG GTC        146
Asp Pro Leu Gln Asp Phe Cys Val Ala Asp Leu Asp Gly Lys Ala Val
             30                  35                  40

TCG GTG AAC GGG CAC ACG TGC AAG CCC ATG TCG GAG GCC GGC GAC GAC        194
Ser Val Asn Gly His Thr Cys Lys Pro Met Ser Glu Ala Gly Asp Asp
         45                  50                  55

TTC CTC TTC TCG TCC AAG TTG GCC AAG GCC GGC AAC ACG TCC ACC CCG        242
Phe Leu Phe Ser Ser Lys Leu Ala Lys Ala Gly Asn Thr Ser Thr Pro
     60                  65                  70

AAC GGC TCC GCC GTG ACG GAG CTC GAC GTG GCC GAG TGG CCC GGT ACC        290
Asn Gly Ser Ala Val Thr Glu Leu Asp Val Ala Glu Trp Pro Gly Thr
 75                  80                  85                  90

AAC ACG CTG GGT GTG TCC ATG AAC CGC GTG GAC TTT GCT CCC GGA GGC        338
Asn Thr Leu Gly Val Ser Met Asn Arg Val Asp Phe Ala Pro Gly Gly
                 95                 100                 105

ACC AAC CCA CCA CAC ATC CAC CCG CGT GCC ACC GAG ATC GGC ATC GTG        386
Thr Asn Pro Pro His Ile His Pro Arg Ala Thr Glu Ile Gly Ile Val
            110                 115                 120

ATG AAA GGT GAG CTT CTC GTG GGA ATC CTT GGC AGC CTC GAC TCC GGG        434
Met Lys Gly Glu Leu Leu Val Gly Ile Leu Gly Ser Leu Asp Ser Gly
        125                 130                 135

AAC AAG CTC TAC TCG AGG GTG GTG CGC GCC GGA GAG ACG TTC CTC ATC        482
Asn Lys Leu Tyr Ser Arg Val Val Arg Ala Gly Glu Thr Phe Leu Ile
    140                 145                 150

CCA CGG GGC CTC ATG CAC TTC CAG TTC AAC GTC GGT AAG ACC GAG GCC        530
Pro Arg Gly Leu Met His Phe Gln Phe Asn Val Gly Lys Thr Glu Ala
155                 160                 165                 170

TCC ATG GTC GTC TCC TTC AAC AGC CAG AAC CCC GGC ATT GTC TTC GTG        578
Ser Met Val Val Ser Phe Asn Ser Gln Asn Pro Gly Ile Val Phe Val
                175                 180                 185

CCC CTC ACG CTC TTC GGC TCC AAC CCC CCC ATC CCA ACG CCG GTG CTC        626
Pro Leu Thr Leu Phe Gly Ser Asn Pro Pro Ile Pro Thr Pro Val Leu
            190                 195                 200

ACC AAG GCA CTC CGG GTG GAG GCC AGG GTC GTG GAA CTT CTC AAG TCC        674
Thr Lys Ala Leu Arg Val Glu Ala Arg Val Val Glu Leu Leu Lys Ser
        205                 210                 215

AAG TTT GCC GCT GGG TTT TAATTTCTAG GAGCCTTCCC TGAAATGATA               722
Lys Phe Ala Ala Gly Phe
    220

ATTATATAAT TCCATATATG CATGCTAGC                                        751
```

(2) INFORMATION FOR SEQ ID NO: 17:

(i) SEQUENCE CHARACTERISTICS:
        (A) LENGTH: 224 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Gly Tyr Ser Lys Thr Leu Val Ala Gly Val Phe Ala Met Leu Leu
 1               5                  10                  15

Leu Ala Pro Ala Val Leu Ala Thr Asp Pro Asp Pro Leu Gln Asp Phe
                20                  25                  30

Cys Val Ala Asp Leu Asp Gly Lys Ala Val Ser Val Asn Gly His Thr
            35                  40                  45

Cys Lys Pro Met Ser Glu Ala Gly Asp Asp Phe Leu Phe Ser Ser Lys
         50                  55                  60

Leu Ala Lys Ala Gly Asn Thr Ser Thr Pro Asn Gly Ser Ala Val Thr
65                  70                  75                  80

Glu Leu Asp Val Ala Glu Trp Pro Gly Thr Asn Thr Leu Gly Val Ser
                85                  90                  95

Met Asn Arg Val Asp Phe Ala Pro Gly Gly Thr Asn Pro Pro His Ile
               100                 105                 110

His Pro Arg Ala Thr Glu Ile Gly Ile Val Met Lys Gly Glu Leu Leu
            115                 120                 125

Val Gly Ile Leu Gly Ser Leu Asp Ser Gly Asn Lys Leu Tyr Ser Arg
        130                 135                 140

Val Val Arg Ala Gly Glu Thr Phe Leu Ile Pro Arg Gly Leu Met His
145                 150                 155                 160

Phe Gln Phe Asn Val Gly Lys Thr Glu Ala Ser Met Val Val Ser Phe
                165                 170                 175

Asn Ser Gln Asn Pro Gly Ile Val Phe Val Pro Leu Thr Leu Phe Gly
            180                 185                 190

Ser Asn Pro Pro Ile Pro Thr Pro Val Leu Thr Lys Ala Leu Arg Val
        195                 200                 205

Glu Ala Arg Val Val Glu Leu Leu Lys Ser Lys Phe Ala Ala Gly Phe
    210                 215                 220
```

(2) INFORMATION FOR SEQ ID NO: 18:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO: 18:

```
Thr Asp Pro Asp Pro Leu Gln Asp Phe Xaa Val Ala Asp Leu Asp Gly
 1               5                  10                  15

Lys Ala Val Ser Val Asn Gly His Thr Xaa Lys Pro Met Ser Glu Ala
                20                  25                  30

Gly Asp Asp Phe Leu Phe
            35
```

(2) INFORMATION FOR SEQ ID NO: 19:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO: 19:

```
Ala Gly Glu Thr Phe Val Ile Pro Arg
1               5
```

(2) INFORMATION FOR SEQ ID NO: 20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

AGCTGGATCC                                                    10

USE OF A DNA SEQUENCE CODING FOR A PROTEIN CAPABLE OF DEGRADING OXALIC ACID AS SELECTION GENE

The invention relates to a novel use of a DNA sequence coding for a protein capable of degrading oxalic acid for selecting plant cells, in particular plant cells which have integrated a gene of interest, and a novel process for selecting, on oxalic acid, cells, calluses or transformed plants.

Since the arrival of the first transgenic plants in 1983, the number of these has enjoyed an accelerated growth. The transformation vectors which have been developed in this period and which are always used, such as, for example, the vector pBIN19 (M. Bevan, 1984, Nucl. Ac. Res., 12, 8711–8721) produce a resistance gene to an antibiotic, kanamycin, as selection gene of transformed plant cells. The use of this mode of selection, generally easy to carry out, cheap and applicable to numerous plant species, has become very widespread in research laboratories.

Since the first field trials, thus out of confinement, of transgenic plants took place in 1986, the use of a resistance gene to an antibiotic as selection gene has been the subject of numerous reviews (cf. particularly F. Casse-Delbart and M. Tepfer, 1990, Biofutur, June, 56–59 as well as J. Bryant and S. Leather, 1992, Tibtech, 10, 274–275). The risk of transmission of the resistance gene of the transgenic plant to a soil bacterium and, subsequently, to a bacteria which is potentially pathogenic for man, although a priori being very slight and still never demonstrated, is not to be neglected (J. A. Heinemann, 1991, TIG, 7, 181–185).

Numerous substitutes for the resistance gene to kanamycin have been proposed (M. Ratner, 1989, Bio-Technology, 7, 337–341) but the majority produce either resistance to another antibiotic (such as, for example, gentamicin, streptomycin, methotrexate or hygromycin), or resistance to a herbicide (such as, for example, bromoxynil or phosphoinothrycin), which raises similar objections. Another approach proposed has been the elimination, after use, of the resistance gene due to a system of homologous recombination (E. C. Dale and D. W. Ow, 1991, Proc. Natl. Acad. Sci. U.S.A., 88, 10558–10562). This system, called the cre/lox system, presents, however, the disadvantage of requiring a subsequent transformation of the transgenic plants to introduce into them the cre gene responsible for the recombination, followed by a self-fertilization of the plants in order to be able to segregate in the descendents this cre gene from the gene of interest. It is thus not simple to use. In addition, this system leaves in the transgenic plants a copy of the lox sequences, which do not have any agronomic interest.

The invention proposes, as selection gene of the transgenic plants, a gene coding for a protein capable of degrading oxalic acid, a phytotoxin produced by numerous species of fungi. This selection gene which remains in the transgenic plants has an agronomic interest because it has a phytoprotective effect with respect to these fungi.

The invention thus relates to the use of a DNA sequence coding for a protein capable of degrading oxalic acid as selection gene for plant cells.

The protein capable of degrading oxalic acid can be an enzyme with decarboxylase activity, such as, especially, the oxalate decarboxylase of *Aspergillus* or of *Collybia velutipes* or preferably an enzyme with oxidase activity, such as, for example, the oxalate oxidase of barley (marketed by Boehringer, ref. 567 698), of sorghum (Chandra S. Pundier, 1991, Phyto-chemistry, 30, 4, p. 1065) or of moss [*Mnium menziesii* (M. F. Laker et al., 1980, Clinical Chemistry, 26, 7, 827)].

A particularly valued protein with oxalate oxidase activity is the protein of sequence [SEQ ID No. 1]:

```
Met Gly Tyr Ser Lys Thr Leu Val Ala Gly Leu Phe Ala Met Leu Leu
1               5                   10                  15

Leu Ala Pro Ala Val Leu Ala Thr Asp Pro Asp Pro Leu Gln Asp Phe
                20                  25                  30

Cys Val Ala Asp Leu Asp Gly Lys Ala Val Ser Val Asn Gly His Thr
                35                  40                  45

Cys Lys Pro Met Ser Glu Ala Gly Asp Asp Phe Leu Phe Ser Ser Lys
            50                  55                  60

Leu Ala Lys Ala Gly Asn Thr Ser Thr Pro Asn Gly Ser Ala Val Thr
65                  70                  75                  80

Glu Leu Asp Val Ala Glu Trp Pro Gly Thr Asn Thr Leu Gly Val Ser
                85                  90                  95

Met Asn Arg Val Asp Phe Ala Pro Gly Gly Thr Asn Pro Pro His Ile
                100                 105                 110

His Pro Arg Ala Thr Glu Ile Gly Ile Val Met Lys Gly Glu Leu Leu
            115                 120                 125

Val Gly Ile Leu Gly Ser Leu Asp Ser Gly Asn Lys Leu Tyr Ser Arg
            130                 135                 140

Val Val Arg Ala Gly Glu Thr Phe Leu Ile Pro Arg Gly Leu Met His
145                 150                 155                 160

Phe Gln Phe Asn Val Gly Lys Thr Glu Ala Ser Met Val Val Ser Phe
                165                 170                 175

Asn Ser Gln Asn Pro Gly Ile Val Phe Val Pro Leu Thr Leu Phe Gly
            180                 185                 190
```

-continued

```
Ser Asn Pro Pro Ile Pro Thr Pro Val Leu Thr Lys Ala Leu Arg Val
        195                 200                 205

Glu Ala Arg Val Val Glu Leu Leu Lys Ser Lys Phe Ala Ala Gly Phe
    210                 215                 220
``` or of sequence having a high degree of homology with the sequence [SEQ ID No. 1].

The sequence [SEQ ID No. 1] is that of wheat germin, a protein induced during the germination of wheat, whose sequence has been described by E. Dratewka-Kos, 1989, J. Biol. Chem., 264, 4896–4900 and B. G. Lane, 1991, J. Biol. Chem., 266, 10461–10469.

A high degree of homology here signifies a homology (ratio between the identical amino acids and the total number of amino acids) of at least 80% of the amino acid sequences, when they are aligned according to maximum homology according to the optimum alignment method of the sequences of Needleman and Wunsch, 1970, J. Mol. Biol, 48, 443–453. This method is particularly used in the UWGCG software of the University of Wisconsin: Devereux et al., 1984, Nucl. Ac. Res., 12, 387–395—GAP option.

An example of a protein having a high degree of homology with the sequence [SEQ ID No. 1] is that of oxalate oxidase of barley whose sequence is described in the patent application WO 92/14824 (this sequence has a homology of 96% with the sequence [SEQ ID No. 1], or that of other oxalate oxidases of cereals close to wheat.

Considering the degeneration of the genetic code, there are a large number of nucleotide sequences coding for the oxalate oxidase of sequence [SEQ ID No. 1]. Among these, the sequence [SEQ ID No. 2] is particularly valued single vector containing the two sequences above, this vector being termed recombinant DNA below.

The sequence of interest is the whole DNA sequence providing an advantage to the plant cells when it is integrated into their genome. It can be, for example, an advantageous regulatory sequence. It can also be a sequence coding for a protein of interest or for a precursor of the latter.

According to a preferred method of carrying out the invention, the sequence of interest confers on plants resistance to pathogenic agents, such as fungi, bacteria, as well as arthropods, particularly insects and nematodes.

Such a sequence of interest can be, for example, a sequence coding for a protein with endochitinase activity or for a precursor of the latter. It is in fact known, as described in the patent application WO92/01792, that such a protein has a phytoprotective effect because it is capable of degrading chitin, a polysaccharide polymer formed from units of N-acetylglucosamine associated by β-1,4 links, which is an important structural compound of the wall of most pathogenic fungi, of the exoskeleton of arthropods, in particular of insects, and of the external covering of eggs and of nematode cysts.

An interesting sequence coding for a protein with endochitinase activity or for a precursor of the latter is that described in the patent application WO92/01792, which codes for a protein comprising the sequence [SEQ ID No. 3]; this sequence [SEQ ID No. 3] corresponds to the sequence [SEQ ID No. 1] of the application WO92/01792.

```
ATGGGGTACT CCAAAACCCT AGTAGCTGGC CTGTTCGCAA TGCTGTTACT AGCTCCGGCC    60

GTCTTGGCCA CCGACCCAGA CCCTCTCCAG GACTTCTGTG TCGCCGACCT CGACGGCAAG   120

GCGGTCTCGG TGAACGGGCA CACGTGCAAG CCCATGTCGG AGGCCGGCGA CGACTTCCTC   180

TTCTCGTCCA AGTTGGCCAA GGCCGGCAAC ACGTCCACCC CGAACGGCTC CGCCGTGACG   240

GAGCTCGACG TGGCCGAGTG GCCCGGTACC AACACGCTGG GTGTGTCCAT GAACCGCGTG   300

GACTTTGCTC CCGGAGGCAC CAACCCACCA CACATCCACC CGCGTGCCAC CGAGATCGGC   360

ATCGTGATGA AGGTGAGCT TCTCGTGGGA ATCCTTGGCA GCCTCGACTC CGGGAACAAG   420

CTCTACTCGA GGGTGGTGCG CGCCGGAGAG ACGTTCCTCA TCCCACGGGG CCTCATGCAC   480

TTCCAGTTCA ACGTCGGTAA GACCGAGGCC TCCATGGTCG TCTCCTTCAA CAGCCAGAAC   540

CCCGGCATTG TCTTCGTGCC CCTCACGCTC TTCGGCTCCA ACCCGCCCAT CCCAACGCCG   600

GTGCTCACCA AGGCACTCCG GGTGGAGGCC AGGGTCGTGG AACTTCTCAA GTCCAAGTTT   660

GCCGCTGGGT TT                                                      672
```

According to a variant of the invention, the DNA sequence coding for a protein capable of degrading oxalic acid can be used in combination with a sequence of interest.

Thus, according to this variant, the invention relates to the use of the DNA sequence coding for a protein capable of degrading oxalic acid for selecting transformed plant cells with a sequence of interest, the transformation being carried out either with the aid of two distinct vectors, one carrying the DNA sequence coding for a protein capable of degrading oxalic acid, the other the sequence of interest, or with a It is particularly appreciated that this sequence codes for a precursor of a protein with endochitinase activity, which comprises, upstream of the sequence [SEQ ID No. 3], the peptide signal of sequence [SEQ ID No. 4]; this peptide signal corresponds to the peptide signal having the sequence [SEQ ID No. 3] described in the application WO92/01792.

It is advantageous then that the peptide signal of sequence [SEQ ID No. 4] be separated from the protein with chitinase activity of sequence [SEQ ID No. 3] by the peptide of sequence [SEQ ID No. 5]; this peptide corresponds to the peptide having the sequence [SEQ ID No. 2] described in the application WO92/01792.

Among the numerous nucleotide sequences which code for a precursor of the protein of sequence [SEQ ID No. 3] comprising, upstream of this, the peptide signal of sequence [SEQ ID No. 4], separated from the protein of sequence [SEQ ID No. 3] by the peptide of sequence [SEQ ID No. 5], the DNA sequence [SEQ ID No. 6] is particularly preferred. This sequence, which corresponds to the sequence [SEQ ID No. 4] described in the application WO92/01792, comprises two introns in positions 443–521 and in positions 676–756.

Another sequence coding for a protein with endochitinase activity or for a precursor of the latter is that of the chitinase of *Aphanocladium album* described in the application EP-A1-531 218, which comprises the sequence [SEQ ID No. 7]. This sequence corresponds to the sequence [SEQ ID No. 1] of the application EP-A1-531 218.

It is particularly appreciated that this sequence codes for a precursor of a protein with endochitinase activity, which comprises, upstream of the sequence [SEQ ID No. 7], the peptide signal of sequence [SEQ ID No. 8]. This peptide signal corresponds to the peptide signal having the sequence [SEQ ID No. 4] of the application EP-A1-531 218.

It is advantageous then that the peptide signal of sequence [SEQ ID No. 8] be separated from the protein with chitinase activity of sequence [SEQ ID No. 7] by the peptide of sequence [SEQ ID No. 9]. This peptide corresponds to the peptide having the sequence [SEQ ID No. 5]described in the application EP-A1-531 218.

Among the numerous nucleotide sequences which code for the protein of sequence [SEQ ID No. 7], a particularly valued sequence is the DNA sequence [SEQ ID No. 10] which corresponds to the sequence [SEQ ID No. 6] described in the application EP-A1-531 218.

Another advantageous sequence of interest which confers on plants resistance to pathogenic agents is that which codes for a protein with β-1,3-glucanase activity or for a precursor of the latter. It is in fact known, as described in the patent application WO-92 16632, that such a protein has a phytoprotective effect because it is capable of degrading β-1,3-glucans, polysaccharide polymers formed from glucose units associated by β-1,3 links sometimes having branchings of β-1,4 or β-1,6 type, which are an important structural compound of the wall of the majority of fungi, and especially of phytopathogenic fungi.

Such an advantageous sequence is that described in the patent application WO 92/16 632, which codes for a protein comprising the sequence [SEQ ID No. 11]. This sequence corresponds to the sequence ($a_1$) described in the application WO92/16 632.

It is interesting that this sequence of interest comprises, immediately downstream of the sequence coding for the sequence [SEQ ID No. 11], the sequence [SEQ ID No. 12] optionally truncated in its carboxy-terminal part by 0 to 27 amino acids. This sequence [SEQ ID No. 12] corresponds to the sequence ($a_4$) described in the application WO 92/16 632.

This sequence of interest thus preferably comprises, immediately upstream of the sequence coding for the sequence [SEQ ID No. 11], a CAA or CAG codon coding for Gln.

A particularly valued sequence of this type is that coding for a protein with β-1,3-glucanase activity or a precursor of the latter which comprises the sequence [SEQ ID No. 13]. This sequence corresponds to the sequence ($a_5$) described in the application WO 92/16 632.

It is particularly appreciated that this sequence codes for a precursor of a protein with β-1,3-glucanase activity which comprises, upstream of the sequence [SEQ ID No. 13] the peptide signal of sequence [SEQ ID No. 14]. This peptide signal corresponds to the peptide signal having the sequence ($a_2$) described in the application WO 92/16 632.

Among the numerous nucleotide sequences which code for the protein of sequence [SEQ ID No. 13], an advantageous sequence is the DNA sequence [SEQ ID No. 15] which corresponds to the sequence ($Na_1$) described in the application WO 92/16 632.

The recombinant DNA defined above, comprising the gene coding for the oxalate oxidase flanked by signals necessary for its expression as well as a sequence of interest, is introduced into the plant cells to be transformed. When the sequence of interest codes for a protein or a precursor of this, it likewise comprises the signals necessary for its expression. The construct containing these sequences can be produced in a unique vector or in different vectors which will be used for the transformation.

The promoter is preferably a strong constitutive promoter, for example the 35S promoter of the cauliflower mosaic virus, or a promoter controlling a specific tissue or organ expression such as the promoter of the small sub-unit of the ribulose 1,5-biphosphate carboxylase-oxygenase which is expressed preferentially in the leaves and very particularly in the tissues of the mesophyll (Kuhlemeier et al., 1987, Ann. Rev. Plant Physiol, 38, 221–257). It is likewise possible to use a specific promoter controlling, for example, an expression in the seeds or in the course of a precise stage of the development of the plant, or a promoter inducible following a thermal shock, a wound or the interaction between the plant and parasites (Kuhlemeier et al., 1987, reference cited above), if an expression of recombinant DNA is sought after in these situations.

The terminator sequence is used, comprising polyadenylation sites, which can be isolated from plant genes or from genes which are expressed in plants, such as, for example, the terminator of the gene of nopaline synthase of *Agrobacterium tumefaciens*.

A bacteria, for example of the type *Escherichia coli*, which contains recombinant DNA defined above with the means allowing its replication can serve for the cloning of this recombinant DNA, and a bacteria capable of infecting a plant with transference of genetic material, for example of one of the type *Agrobacterium rhizogenes* and *Agrobacterium tumefaciens*, which contains this DNA in a context allowing its replication, can serve to transform plant cells. The transformation of plant cells by the recombinant DNA above can likewise be effected by another biological method such as the pollen tube route (Zhong-xun Luo et al., Plant Molec. Biol. Rep., 1988, 6, 165–176), the direct transformation of germinating seeds (Toepfer R. et al., 1989, The Plant Cell., 1, 133–139) or by a physical method such as the use of polyethylene glycol, of electroporation (Chistou P. et al., 1987, Proc. Ntl. Acad. Sci. U.S.A., 84, 3662–3699) or of bombardment with the aid of microprojectiles (Klein T. M. et al., 1988, Proc. Ntl. Acad. Sci. U.S.A., 85, 8502–8505).

The invention thus also relates to a plant cell, characterized in that it is transformed by recombinant DNA defined above, with the necessary means for the expression of the protein capable of degrading oxalic acid and of the protein of interest or of the precursor of the latter; such a cell can be selected on a medium containing oxalic acid. This plant cell can arise from a type of large crop, such as, for example, maize, soya, beetroot, wheat, barley, poppy, rape, sunflower, lucerne and sorghum, from a flower species, such as, for example, the rose, carnation or gerbera or from a culinary species, such as the carrot, tomato, lettuce, chicory, pepper, melon and cabbage. Species particularly valued are the rape *Brassica napus*, the sunflower *Helianthus annuus* and the tobacco *Nicotiana tabacum*.

The transformation stage which affects one or more cells is followed by a multiplication stage of these transformed cells in such a way as to obtain calluses, which can give rise to transformed plants by organogenesis or embryogenesis processes.

The invention thus also relates to a plant or a plant part, characterized in that it contains recombinant DNA defined above, with the necessary means for the expression of the gene coding for the protein capable of degrading oxalic acid and of the gene coding for the protein of interest or of the precursor of the latter and in that this has been selected on a medium containing oxalic acid. A plant part particularly valued is the part capable of forming a complete new plant, especially after sowing, digging in or transplanting, or of producing seeds. Such a part is, for example, a grain, a kernel, a seed, a cutting or a layer. These plants can be, more particularly, of the species *Nicotiana tabacum*, *Helianthus annuus* and *Brassica napus*.

The protein capable of degrading oxalic acid can be an enzyme with decarboxylase activity, such as, especially, the oxalate decarboxylase of *Aspergillus* or of *Collybia velutipes* or preferably an enzyme with oxidase activity, such as, for example, the oxalate oxidase of barley (marketed by Boehringer, ref. 567 698), of sorghum (Chandra S. Pundier, 1991, Phytochemistry, 30, 4, p.1065) or of moss (*Mnium menziesii*) (M. F. Laker et al., 1980, Clinical Chemistry, 26, 7, 827). A particularly valued protein with oxalate oxidase activity is the protein of sequence [SEQ ID No. 1], or a sequence having a high degree of homology with the sequence [SEQ ID No. 1]. This is advantageously coded by the DNA sequence [SEQ ID No. 3].

Oxalic acid is a phytotoxin produced by numerous pathogenic fungi, such as, especially, *Sclerotinia sclerotiorum* (B. Grezes-Besset, 1988, Doctoral Thesis, Université Paul Sabatier, Toulouse, as well as G. Goday et al., 1990, Physiological and Molecular Plant Pathology, 37, 179–191), *Sclerotium rolfsii* (D. F. Bateman et al., 1965, Phytopathology, 68, 1597–1599), *Aspergillus niger* (I. A. S. Gibson, 1953, Transactions British Mycological Society, 36, 198–209), *Cristulariella pyramidalis* (P. Kurian et al., 1979, Phytopathology, 69, 712–714) and *Cryphonectria parasitica* (A. R. Bennett et al., 1990, Mycologia, 358–363).

The invention likewise relates to a process for selecting, on oxalic acid, cells, calluses or plants transformed by a recombinant DNA defined above, characterized in that, in the selection medium, the calcium is in soluble form.

The plants can arise from a species of large crop, such as, for example, maize, soya, beetroot, wheat, barley, poppy, rape, sunflower, lucerne and sorghum, from a flower species, such as the rose, carnation or gerbera or from a culinary species, such as the carrot, tomato, lettuce, chicory, pepper, melon and cabbage. Particularly valued species are the rape *Brassica napus*, the sunflower *Helianthus annuus* and the tobacco *Nicotiana tabacum*.

The selection medium comprises oxalic acid and all the elements necessary for the multiplication and the differentiation of plant cells and especially of calcium, which is indispensable for their development, which must then remain available. In the presence of oxalic acid, calcium has a tendency to associate with the latter to form an insoluble oxalate salt, which makes it unavailable to the plant cells. It is thus necessary for the selection medium to contain agents allowing calcium to be kept in soluble form.

Preferably, these agents are chelating agents having an affinity for calcium which is higher than that of oxalic acid. Of course these must not, in addition, be toxic to the cells.

Examples of chelating agents having an affinity for calcium higher than that of oxalic acid are EDTA and EGTA. In the case of the sunflower, EGTA is a particularly valued chelating agent.

Thus, according to another aspect, the invention relates to a process for selecting, on oxalic acid, calluses or plants transformed by a DNA sequence coding for a protein capable of degrading oxalic acid, which consists in cultivating the calluses or the plants on a medium containing oxalic acid and calcium in the presence of a chelating agent having an affinity for calcium which is higher than that of oxalic acid.

According to a preferred variant, the plants are transformed with a DNA sequence coding for a protein capable of degrading oxalic acid associated with a sequence of interest such as that defined above, in particular a sequence coding for a protein of interest.

The invention will be better understood with the aid of the account below, divided into sections, which comprises experimental results and a discussion of these. Certain of these sections relate to experiments carried out with the aim of accomplishing the invention, others to examples of accomplishment of the invention, given, of course, in a purely illustrative capacity.

In this experimental part, the clone gf-2.8 of wheat germin described by B. G. Lane et al., 1991, J. Biol. Chem., 226-10461–10469 is used; the genomic DNA sequence of this clone is the sequence [SEQ ID No. 16] and the peptide sequence translated is the sequence [SEQ ID No. 17].

A large part of the whole of the techniques below, which are well known to the person skilled in the art, is set out in detail in the works of Sambrook et al.: "Molecular Cloning: a Laboratory Manual", published in 1989 by the publishers Cold Spring Harbor Press in New York (2nd edition), and in the work of Gelvin et al.: "Plant Molecular Biology Manual", published in 1988 by the publishers Kluwer Academics.

SECTION 1: PURIFICATION AND PARTIAL CHARACTERIZATION OF OXALATE OXIDASE OF BARLEY

1) Purification of Oxalate Oxidase of Barley

An oxalate oxidase of barley has been purified to homogeneity starting from a commercial preparation enriched in oxalate oxidase activity (Boehringer, ref. 567 698) prepared starting from germinating barley grains. The protein is purified according to the protocol described below:

STAGE 1

The lyophilized commercial preparation is solubilized in water and then equilibrated in a 10 mM acetate buffer of pH 5.2 by passage through a ready-to-use Sephadex G25 minicolumn (NAP 10-Pharmacia). This extract is fractionated by chromatography on a synthetic polymer ion-exchange column (Mono S HR5/5 column from Pharmacia). After applying the sample, the unretained proteins are eluted by the 10 mM sodium acetate buffer of pH 5.2. The proteins retained on the column are eluted by a 10 to 500 mM linear gradient of sodium acetate buffer of pH 5.2.

The eluate is analysed on line by its absorbance at 280 nm and the collected fractions are characterized: protein contents measured by the colorimetric technique of Bradford (1976, Anal. Biochem., 72, 248–252), oxalate oxidase activity measured according to the technique of Suguira et al., 1979, Chem. Pharm. Bull., 79, 2003–2007, described at point 2) below. Each fraction is characterized, after electrophoresis under denaturing conditions (SDS) and coloration with silver, by its electrophoretic mobility compared with reference proteins.

STAGE 2

The fractions have oxalate oxidase activity and, eluted at a sodium acetate concentration of between 200 mM and 275 mM, are collected and then concentrated by centrifugation in a Centricon-10 system (Amicon-ref. 4205). The extract is then fractionated by exclusion chromatography on a Superdex 75 column (Pharmacia). The fractions collected are analysed according to the methods described in Stage 1.

At the end of the purification, a unique protein is obtained which has an oxalate oxidase activity and an apparent molecular weight of 26±3 kDa (molecular weight determined after electrophoresis on 15% polyacrylamide gel in the presence of SDS and visualisation with silver).

2) Measurement of the Oxalate Oxidase Activity

The oxalate oxidase activity is measured according to the method described by Suguira et al., 1979, Chem. Pharm. Bull., 79, 2003–2007, and summarized below. The enzymatic extract is incubated in the presence of 75 μl of sodium oxalate (0.18% in a 100 mM succinate buffer of pH 4.0) and of 100 mM succinate buffer of pH 4.0, in quantities sufficient to have a volume of reaction mixture equal to 1.5 ml.

After incubation of the reaction mixture at 37° C. for 10 minutes, 100 μl of 1 M tris buffer of pH 8.9, then 1 ml of reagent prepared at the same time and made up of: 8 mg of 4-aminoantipyrine, 6 mg of horseradish peroxidase (Sigma, ref. P8250) and 80 μl of dimethylaniline prepared in 100 ml of 0.1 M phosphate buffer of pH 7.0 are added successively.

The enzymatic activity is estimated by the spectrophotometric measurement of the absorbance at 530 nm. It is expressed in units of oxalate oxidase/mg of protein (one unit of oxalate oxidase (U oxox) is the quantity of enzyme which converts 1 μmol of oxalate into hydrogen peroxide in 1 minute at 37° C. and at pH 3.8).

3) Characterization of the Purified Protein a) Preparation of Polyclonal Antibodies 25 μg of the barley protein purified to homo-geneity and having an oxalate oxidase activity are injected into a rabbit in 500 μl of complete Freund's adjuvant (Sigma, ref. F5881).

Three booster injections of 25 μg in incomplete Freund's adjuvant (500 μl) (Sigma ref. F5506) were carried out at 3 week intervals. The immune serum was taken 3 weeks after the last injection.

This immune serum specifically recognises oxalate oxidase. It allows this protein to be revealed by the Western blot technique (described in Section 2 4) b) starting from a total protein extract of germinating barley embryos.

b) Determination of the Partial Sequence of the Oxalate Oxidase

A sample of the protein of 26±3 kDa having an oxalate oxidase activity is treated with cyanogen bromide and the oligopeptides liberated are separated by inverse phase HPLC on a C4 Brownlee column. The N-terminal sequence of the protein as well as that of an internal peptide are determined using a protein sequencer (Model 470A, Applied Biosystems, U.S.A.) equipped with a chromatograph (Model 120A, Applied Biosystems) which continuously analyses the phenylthio-hydantoic derivatives formed after each degradation cycle.

The amino-terminal sequence determined is the following sequence [SEQ ID No. 18]:

```
Thr Asp Pro Asp Pro Leu Gln Asp Phe Xaa Val Ala Asp Leu Asp Gly

Lys Ala Val Ser Val Asn Gly His Thr Xaa Lys Pro Met Ser Glu Ala

Gly Asp Asp Phe Leu Phe
```

Xaa being an undetermined amino acid.

The sequence of an internal peptide is the following sequence [SEQ ID No. 19]:

Ala Gly Glu Thr Phe Val Ile Pro Arg

After comparison with the bank of known protein sequences (Swiss-Prot bank) using the GAP option of the UWGCG software of the University of Wisconsin: Devereux et al., 1984, Nucl. Acids Res., 12, 387–395, a homology of at least 94% is found with the sequence of a wheat protein induced in the course of germination, germin, described by Lane et al., 1991, J. Biol. Chem., 226, 10461–10469.

SECTION 2: TRANSFORMATION OF TOBACCO BY THE WHEAT GERMIN GENE, SELECTION ON OXALIC ACID OF THE CALLUSES AND OF TRANSGENIC PLANTS

1) Construction of a Transformation Vector a) Preparation of the Sequence Coding for Wheat Germin The 745 base pair DNA fragment HindIII-SphI of the clone gf-2.8 described by B. G. Lane et al., (1991, J. Biol. Chem., 226, 10461–10469) carrying the sequence coding for wheat germin was purified by electrophoresis on agarose gel followed by extraction by means of the "Geneclean" kit (Bio 101, ref. 3105) according to the procedure of the manufacturer. This fragment comprises 19 base pairs upstream of the ATG initiator as well as 54 base pairs downstream of the stop codon. This fragment was inserted with the aid of the DNA T 4 ligase between the sites HindIII and SphI of the multiple cloning site of a pTZ19R vector (marketed by Pharmacia), whose BamHI site had been destroyed by filling using Klenow polymerase, according to the methods which are well known to the person skilled in the art. The plasmid thus created is called plasmid pPHO96. The HindIII site present in this plasmid is then opened, and a new BamHI site is recreated by addition of an oligonucleotide of following sequence [SEQ ID No. 20]: AGCTGGATCC The vector obtained, called plasmid pPH098, is cloned in the strain *E.coli* JM 109 (Clontech). After verification of the nucleotide sequence of the cloned fragment, the coding part is repurified in the form of the restriction fragment BamHI- SacI of 789 base pairs. This fragment contains the sequence coding for the peptide signal, as well as that coding for the mature germin, such as are described by B. Lane et al., 1991, J. Biol. Chem., 226, 10461–10469.

b) Preparation of the Promoter Sequence Comprising the 35S Promoter of the Cauliflower Mosaic Virus Starting from the plasmid pBI121 (Clontech), by cleavage with the aid of the endonucleases HindIII and BamHI, then electrophoresis on agarose gel, the HindIII-BamHI fragment of approximately 900 base pairs, containing the 35S promoter of the cauliflower mosaic virus, is isolated. This fragment is cut again by HindIII. The fragment of approximately 410 base pairs, carrying the BamHI site, is treated by DNA T4 ligase in the presence of a HindIII linker (synthetic sequence containing a HindIII site). After cutting by the endonuclease HindIII and electrophoresis on agarose gel, the resulting HindIII-BamHI fragment, of approximately 420 base pairs, is isolated and purified.

c) Preparation of the Terminator Sequence Comprising the Terminator of the Nopaline Synthase (NOS) Gene of *Agrobacterium Tumefaciens*

Starting from the plasmid pBI121 (Clontech), by cutting with the aid of the restriction enzymes SacI and EcoRI, then electrophoresis on agarose gel, a fragment of approximately 250 base pairs, containing the terminator of the nopaline synthase gene, was isolated.

d) Cloning in the Binary Vector pBIN19

The promoter sequence (cf. above 1)b)), the sequence coding for germin (cf. above 1) a)) and the terminator sequence (cf. above 1)c)) were ligated into the binary vector pBIN19 (Bevan, 1984, Nucl. Acid Res., 12, 8711–8721) with the aid of DNA T4 ligase, and opened with the aid of the endonucleases HindIII and EcoRI. This vector carries two resistance genes to kanamycin, one being able to express itself in bacteria, the other situated immediately upstream of the complete recombinant gene being able to be transferred to plant cells. This resistance gene to kanamycin will serve to verify that the regenerated plantlets obtained after selection on oxalic acid with the aid of the gene coding for oxalate oxidase are effectively transformed.

The vector obtained, called pPH100, is cloned in the strain *E. coli* HB101 (Clontech).

2) Transformation of *Agrobacterium Tumefaciens*

The transformation is carried out according to the freezing-thawing method described in Plant Molecular Biology Manual (Gelvin et al., op. cit.) and summarized below.

Competent cells of *Agrobacterium tumefaciens* (LBA 4404 strain, Clontech) are prepared by rapid cooling in ice of a culture in the exponential growth phase. The bacteria are then resuspended in a 20 mM solution of $CaCl_2$. Aliquot parts of this suspension are distributed in Eppendorf tubes, then frozen in liquid nitrogen.

1 μg of pPH100 plasmid is added to the frozen cells, contained in an Eppendorf tube. The suspension is then incubated at 37° C. for 5 min; 1 ml of Luria medium (Gibco) is then added and the tube is incubated at 28° C. for 4h. Aliquot parts are spread on Petri dishes containing a minimum agar medium, described in Plant Molecular Biology Manual (op. cit.) in the presence of 100 mg of rifampicin and 25 mg/l of kanamycin. Under these conditions, only the colonies of *Agrobacterium tumefaciens* which have integrated the plasmid pPH100 grow. These contain the chimeric gene in a context allowing its replication.

The resistance to the two antibiotics of the selected colonies is verified by transplanting these on the same selection medium twice in succession. The presence of the chimeric gene associating the 35S promoter with the coding part of wheat germin in *Agrobacterium tumefaciens* is verified by the Southern Blot method on a total DNA preparation (lysis of the cells, purification of DNA by extraction with the aid of the mixture phenol/chloroform, according to the procedure described by Gelvin in the work cited above, cutting of the purified DNA with the aid of restriction enzymes, electrophoresis on agarose gel, transfer to membrane and hybridization, according to the techniques which are well known to the person skilled in the art).

3) Transformation of the Tobacco

*Nicotiana tabacum* tobacco cultivated in vitro was infected by *Agrobacterium tumefaciens* containing the plasmid pPH100 according to the procedure of Horsch et al., which is well known to the specialist (Horsch R. B. et al., 1985 Science 227, 1229–1231), whose principle stages are explained below.

Axenic plant leaf discs of *Nicotiana tabacum* tobacco (Wisconsin Havana 38 variety) are incubated in a culture of *A. tumefaciens* containing the plasmid pPH100. The discs, drained on Whatman paper, are cultured on culture media in Petri dishes in order to multiply the transformed cells so as to obtain calluses. These calluses are then transferred onto medium containing cefotaxime at 500 μg/ml which is intended to decontaminate the plant tissues (elimination of *Agrobacterium tumefaciens*) and kanamycin at 100 μg/ml to select the transgenic material. Transformed shoots develop from these calluses; the plants which result from them are transferred to greenhouses.

4) A Demonstration of the Expression of the Germin Gene in Transgenic Tobacco a) Preparation of Protein Extracts of Transformed Tobacco and of Control Tobacco The tissue fragments (calluses and plant leaves) were frozen in liquid nitrogen, powdered and stored at −20° C.

To carry out electrophoreses, the oxalate oxidase is extracted directly from the plant powder by the Laemmli loading buffer (reference below).

For the determinations of oxalate oxidase activity, the enzymatic extract is prepared by suspending plant powder in a 0.05 M succinate buffer, pH 4.

For the protein determinations, the plant extract, suspended in the above succinate buffer, is centrifuged at 10,000 g for 5 min.

The concentration of total proteins is determined on the supernatants, below called crude protein extracts, following the technique of Bradford (Bradford M. M., 1976, Anal. Biochem., 72, 248–254).

b) Immunodetection of Oxalate Oxidase (Western blot) in the Calluses and in the Plants The crude protein extracts are submitted to a Western blot, a technique, which is well known by the person skilled in the art and described by H. Towbin et al., Proc. Ntl. Acad. Sci. U.S.A., 76, 1979, 4350–4354, which comprises the following stages:

denaturation by heating to 100° C. for 10 min in a buffer, termed loading buffer, made up of 0.125 M tris, pH 6.8, 4% SDS, 0.002% Bromophenol Blue, 20% glycerol and 10% β-mercaptoethanol (according to the procedure described by Laemmli U. K., 1970, Nature, 227, 680–685), followed by centrifugation at 10,000 g;

electrophoretic separation of the different proteins contained in the solubilizate according to the procedure described by Laemmli (ref. above);

electrotransfer of the said proteins contained in the gel onto a PVDF membrane (according to the technique of H. Towbin et al., 1979, Proc. Natl. Acad. Sci. U.S.A. 4350–4354).

Immunodetection is carried out according to a procedure which comprises the following stages:

saturation of the PVDF (polyvinylidene fluoride) membrane onto which the proteins have been transferred by incubation for at least 2 h at 37° C. in a 3% gelatin solution in phosphate-buffered saline containing 0.05% of Tween 20 detergent.

Incubation (for 1 h at 37° C. ) in the presence of the immune serum prepared above (containing the polyclonal antibodies recognizing the recombinant protein), diluted to 1/10,000 in phosphate-buffered saline.

3 washes in phosphate-buffered saline containing 0.05% of Tween 20 detergent.

The antigen-antibody complex is then visualized with the aid of a streptavidin-biotin system conjugated to alkaline phosphatase with the Amersham RPN 23 kit ("Blotting detection kit"), used according to the instructions of the manufacturer.

The blot obtained shows, for the calluses and for the tobacco plant leaves transformed by the plasmid pPH100, the presence of a protein of apparent molecular weight of approximately 26±3 kDa, recognized by the polyclonal antibodies prepared in Section 1 3)a) and absent from the calluses and from the control tobacco plant leaves. This protein has the same apparent molecular weight as the purified oxalate oxidase obtained in Section 1.

c) Demonstration of the Oxalate Oxidase Activity of Wheat Germin Expressed in Tobacco The oxalate oxidase activity of 6 extracts of calluses and of tobacco plant leaves transformed by the plasmid pPH100 is measured according to the method of Suguira et al., described in Section 1. The results are gathered together in Table I below:

TABLE I

Oxalate oxidase activity measured in different transgenic tobaccos

|  | Control | Calluses Transgenic | | | | | Leaves | |
|---|---|---|---|---|---|---|---|---|
|  |  |  |  |  |  |  | Control | Transgenic |
| No. of sample | W38 | 2 | 26 | 65 | 81 | 86 | W38 | 400 |
| Activity (U oxox/ml of extract) | 1.0 | 10.5 | 10.1 | 16.0 | 2.8 | 3.0 | 0.0 | 5.4 |

W38 = untransformed control tobacco

It is noted by reading the table above that the transgenic tobacco (calluses or leaves) has a significantly higher oxalate oxidase activity than that of the control tobacco.

5) Selection on Oxalic Acid of the Regenerants a) Selection Procedure

Axenic plant leaf discs of Nicotiana tabacum tobacco (Wisconsin Havana 38 variety) are incubated in a culture of A. tumefaciens containing the plasmid pPH100. The discs, which are drained on Whatman paper, are cultured on culture media in Petri dishes in order to multiply the transformed cells so as to obtain calluses. After three days, the leaf discs are rinsed in 80% ethanol and then in Murashige and Skoog agar medium (1962, Physiol. Plant. 15, 473) containing 500 μg/ml of cefotaxime. They are then transferred to a medium containing oxalic acid in order to select the cellular aggregates expressing oxalate oxidase.

b) Method of Preparation of the Culture Media

As oxalic acid associates with calcium to form an insoluble calcium oxalate salt, the selection medium must be prepared according to a procedure allowing the calcium to be kept in a soluble form which can be used by the plant cells despite the presence of oxalic acid.

Preparation of Solution A

For each concentration, 50 ml of a solution of oxalic acid concentrated 20 times with respect to the final concentration expected, are adjusted to pH 5.8 with a 3M solution of potassium hydroxide (KOH). The solution is adjusted to 100 ml with deionized water, sterilized by filtration through a 0.45 μm filter, then maintained at a temperature of 50° C. until use.

Preparation of Solution B 258 mg of EGTA (ethylene glycol bis-(β-aminoethyl ether)N,N,N',N'-tetraacetic acid) (Sigma, ref. E. 4378) are dissolved in 100 ml of deionized water. The EGTA is solubilized by adjusting the pH to 10.0 with a solution of 10 M KOH. 100 mg of $CaCl_2.2H_2O$ are then added and the pH of the solution is adjusted to 5.8 with a 2 M HCl solution. The volume is adjusted to 150 ml and then the solution is sterilized by passing through a 0.45 μm filter.

Incorporation of the Calcium and the Oxalate in the Culture Medium 750 ml of Murashige and Skoog agar culture medium (1962, Physiol. Plant. 15, 473) without calcium chloride, concentrated 1.33 times, are autoclaved for 20 min at 120° C. The temperature is then lowered to 50° C. and the solutions A and B are incorporated into this medium. After homogenization of the solution, the medium is poured into Petri dishes.

c) Determination of the Amount of Oxalic Acid to be Used for Selection

A range of sensitivity to oxalic acid of non-transgenic tobacco calluses (Wisconsin Havana 38) was established. The culture media were prepared according to the procedure described above. For each concentration of oxalic acid, 4 dishes containing 25 calluses of 2 mm diameter and an average weight of 10 mg were cultured. The results, expressed in % by weight inhibition of growth with respect to control calluses, are shown in Table II below:

TABLE II

Inhibition of the growth in weight of tobacco calluses by oxalic acid

| Oxalic acid conc. (µg/ml) | 0 | 40 | 60 | 80 | 120 | 180 | 270 |
|---|---|---|---|---|---|---|---|
| Growth in weight inhibition | 0% | 0% | 12% | 19% | 51% | 89% | 99% |

Taking the above results into account, the selection dose chosen is 270 µg/ml (3 mM).

d) Use of the Gene Coding for Oxalate Oxidase as Selection Gene of the Transformants After transformation and induction of callogenesis, the tobacco leaf discs are transferred to a medium containing 270 µg/ml of oxalic acid. At this concentration, the calluses expressing oxalate oxidase do not show a different growth from the control growing on a medium devoid of oxalic acid and are capable of surviving and of producing transgenic plants. The fact that the regenerated plantlets are indeed transgenic is verified by their resistance to kanamycin (second selection gene carried by the plasmid pPH100). Of 29 plants selected on oxalic acid, 28 are equally resistant to kanamycin.

The selection on oxalic acid thus allowed transformant calluses as well as transgenic plants to be selected.

SECTION 3: TRANSFORMATION OF THE SUNFLOWER BY THE WHEAT GERMIN GENE, SELECTION OF THE CALLUSES ON OXALLIC ACID

1) Transformation of the Sunflower

Obtainment of Transformed Sunflower Calluses

Immature sunflower seeds are selected on the flower head of sunflower plants of the well known HA89 line, which has been studied especially by the P. J. Goyne et al., Journal Article No. 1534 of the North Dakota State Univ. Agric. Exp. Stn. Fargo ND-58105 and by M. F. Geriani, Plant Cell Physiol, 33, 2, 157–164. These seeds are sterilized on the surface for 30 min in a solution of 2% calcium hypochlorite, then rinsed with sterile distilled water.

The immature embryos are selected on these seeds and cultured on the medium I (Table III) for 14 days at 25° C. and in darkness. These embryos are then cultured for 10 days on the medium II at 25° C. with a 16 h day/8 h night photoperiod.

The embryos are then cut in two at the level of the embryonal axis and soaked for 10 min in a suspension of *Agrobacterium tumefaciens* containing the binary vector pPH100 (cf. Sections 2.1 and 2.2). This suspension is obtained by culture of this bacteria for 15 h in the Luria liquid medium.

The embryos are then drained on sterile filter paper and then recultured on the medium II in darkness for 3 days. The embryos are then briefly rinsed with the Murashige and Skoog liquid medium (Murashige and Skoog, 1962, Physiol. Plant 15:473) containing 500 mg/l of the antibiotic cefotaxime. They are then drained on sterile filter paper and cultured on the medium III containing 250 mg/l of cefotaxime, 250 mg/l of carbenicillin and 50 mg/l of paromomycin. This culture takes place at 25° C. with a 16 h day/8 h night photoperiod; the plant tissues as well as the calluses developing on their surface are transplanted every 21 days on the same medium.

TABLE III

Composition of the different media used to obtain transformed sunflower plants

| Composition mg/l | Medium I | Medium II | Medium III |
|---|---|---|---|
| $KNO_3$ | 2500 | 2500 | 1900 |
| $NH_4NO_3$ | — | — | 1650 |
| $CaCl_2.2H_2O$ | 150 | 150 | 440 |
| $MgSO_4.7H_2O$ | 250 | 250 | 370 |
| $KH_2PO_4$ | — | — | 170 |
| $(NH_4)_2SO_4$ | 134 | 134 | — |
| $NaH_2PO_4.H_2O$ | 150 | 150 | — |
| $MnSO_4.H_2O$ | 10 | 10 | — |
| $ZnSO_4.7H_2O$ | 2 | 2 | 8.6 |
| $H_3BO_3$ | 3 | 3 | 6.2 |
| KI | 0.75 | 0.75 | 0.83 |
| $CuSO4.5H_2O$ | 0.025 | 0.025 | 0.025 |
| $Na_2MoO_4.2H_2O$ | 0.25 | 0.25 | 0.25 |
| $CaCl_2.6H_2O$ | 0.025 | 0.025 | 0.025 |
| $MnSO_4.4H_2O$ | — | — | 22.3 |
| $Na_2EDTA$ | 37.3 | 37.3 | 37.3 |
| $FeSO_4.7H_2O$ | 27.8 | 27.8 | 27.8 |
| Nicotinic acid | 1 | 1 | 0.5 |
| Thiamine HCl | 10 | 10 | 0.1 |
| Pyridoxine HCl | 1 | 1 | 0.1 |
| Myo-inositol | 4000 | 4000 | 100 |
| L-Alanine | 1000 | 1000 | — |
| L-Glutamine | 800 | 800 | — |
| L-Serine | 160 | 160 | — |
| L-Tryptophan | 50 | 50 | — |
| L-Cysteine | 10 | 10 | — |
| Ca D-pantothenate | — | — | 0.8 |
| Folic acid | — | — | 0.1 |
| Choline chloride | — | — | 0.1 |
| 4-Aminobenzoic acid | — | — | 0.05 |
| Riboflavin | — | — | 0.05 |
| Sucrose | 120,000 | 60,000 | 30,000 |
| 2,4-Dichlorophenoxyacetic acid | 2 | — | — |
| 6-Benzylaminopurine | — | 0.4 | — |
| Kinetinn | — | — | 1 |
| Agar | 7000 | 7000 | 7000 |
| pH | 5.7 | 5.8 | 5.7 |

2) Demonstration of the Expression of the Germin Gene in the Transgenic Sunflower a) Preparation of the Protein Extracts Takes place in a manner identical to that described in Section 2 4) a).

b) Immunodetection of the Oxalate Oxidase (Western Blot) in Calluses

Immunodetection, carried out according to the procedure described in Section 2 4)b), demonstrates, in sunflower calluses and leaves transformed by the plasmid pPH100, the presence of a supernumerary protein of apparent molecular weight of approximately 26±3 kDA. This protein, which is absent from calluses and leaves of control plants, has the same apparent molecular weight as the purified oxalate oxidase obtained in Section 1.

Oxalate Oxidase Activity of the Wheat Germin Expressed in the Sunflower

The oxalate oxidase activity of 5 protein extracts of sunflower calluses transformed by the plasmid pPH100 is measured according to the method of Suguira et al., described in Section 1. The results show a significantly higher oxalate oxidase activity to that of the control extract.

TABLE IV

Oxalate oxidase activity of transgenic sunflower calluses

| No. of the callus | Untransformed control | 17 | 18 | 19 | 20 | 21 |
|---|---|---|---|---|---|---|
| Units OxOx/mg prot/min | 0.0 | 9.5 | 0.7 | 0.8 | 0.6 | 1.4 |

3) Selection of the Transgenic Calluses on Oxalic Acid

The selection of the transgenic calluses is carried out by culturing the plant material resulting from the medium III (cf. above 1) on a Murashige and Skoog selection medium prepared according to the procedure described in Section 2 5) b).

The determination of the selection dose to be applied in the course of the culture of sunflower calluses is made according to the method described in Section 2 5)c), this method being applied to non-transgenic sunflower calluses obtained from immature embryos. The results are shown in Table V:

TABLE V

Inhibition of the growth in weight of the sunflower by oxalic acid

| Oxalic acid conc. ($\mu$g/ml) | 0 | 40 | 70 | 90 | 140 | 180 | 235 | 270 |
|---|---|---|---|---|---|---|---|---|
| Growth in weight inhibition | 0% | 0% | 0% | 0% | 42% | 92% | 97% | 99% |

The dose of oxalic acid allowing the selection to be carried out is 270 $\mu$g/ml (3 mM). At this concentration, the calluses expressing oxalate oxidase do not show inhibition of growth.

SECTION 4: USE OF THE SELECTION ON OXALIC ACID TO OBTAIN TRANSGENIC PLANTS POSSESSING A GENE OF INTEREST CODING, FOR EXAMPLE, FOR A PROTEIN WITH ENDOCHITINASE ACTIVITY

1) Construction of the Transformation Vector a) Preparation of the Fragment Carrying the Gene Coding for Oxalate Oxidase The fragment HindIII-EcoRI of approximately 1420 bp of the plasmid pPH100 described in Section 2 d) is purified and recloned in a pUC19 vector according to the methods well known to the person skilled in the art. This plasmid is then linearized using the restriction endonuclease EcoRI and the sticky end is made up by means of the Klenow fragment. Then, after cutting by the HindIII endonuclease, the HindIII-free end fragment is purified.

b) Preparation of the Fragment Carrying a Hybrid Gene Coding for a Protein with Endochitinase Activity The fragment HindIII-EcoRI arising from the plasmid pBR1 described in the patent application WO92/01792 Example 1 and containing a chimeric gene coding for a protein with endochitinase activity which comprises the 35S promoter, a sequence coding for a tomato-tobacco hybrid chitinase and the NOS terminator is purified, recloned in the vector pUC19, then the HindIII site is destroyed in a conventional manner. The free end-EcoRI fragment is purified.

c) Preparation of a Transformation Vector of Plants Not Comprising a Resistance Gene to Kanamycin The fragment NheI-HindIII comprising the part coding for the resistance gene to kanamycin is eliminated from the T-DNA of the plasmid pBIN19 (cf. Section 2 1 d). The use, according to the methods well known by the person skilled in the art, of the oligonucleotides CTAGCA and AGCTTG allows the plasmid to be recircularized recreating the restriction sites NheI and HindIII. The resulting plasmid is then linearized by the restriction endonucleases HindIII and EcoRI.

c) Assembly of the Transformation Vector

With the aid of the DNA ligase T4, the gene coding for oxalate oxidase (obtained in a) above) and the chimeric gene coding for a protein with chitinase activity (obtained in b) above) were ligated in a binary vector pBIN19 in which the resistance gene to kanamycin expressed in plants (obtained in c) above) has been eliminated.

The vector obtained, called pPH106, is cloned in the strain *E.Coli* HB101 (Clontech).

2) Transformation of *Agrobacterium Tumefaciens*

The transformation is carried out according to the method described in Section 2 2).

3) Transformation of the Tobacco

*Nicotiana tabacum* tobacco cultured in vitro is infected with *Agrobacterium tumefaciens* containing the plasmid pPH106 according to the procedure of Horsch et al., which is well known to the person skilled in the art, (Horsch R. B. et al., 1985 Science 227, 1229–1231), whose principle stages are explained below.

Axenic plant leaf discs of *Nicotiana tabacum* tobacco (Wisconsin Havana 38 variety) are incubated in a culture of *A. tumefaciens* containing the plasmid pPH106. The discs, which are drained on Whatman paper, are cultured on culture media in Petri dishes in order to multiply the transformed cells so as to obtain calluses. After 48 hours, the discs are rinsed in 80% ethanol and then in Murashige and Skoog agar medium (1962, Physiol. Plant. 15, 473) containing 500 $\mu$g/ml of cefotaxime. They are then transferred for 3 days to medium containing 500 $\mu$g/ml of cefotaxime which is intended to decontaminate the plant tissues (elimination of the *Agrobacterium tumefaciens*).

4) Selection on Oxalic Acid of the Regenerants

After transformation and induction of callogenesis, the tobacco leaf discs are transferred onto a medium containing 270 $\mu$g/ml of oxalic acid prepared according to the method described in Section 2 5)b). Only the transgenic calluses expressing the oxalate oxidase gene, thus capable of degrading oxalic acid, are capable of surviving and of producing transgenic plants.

5) Demonstration of the Expression of the Protein with Endochitinase Activity in Transgenic Tobaccos Selected on Oxalic Acid a) Preparation of the Crude Protein Extracts of Transformed Tobacco This preparation is carried out according to the method described in Section 2 4)a).

b) Demonstration of the Chitinase Hybrid by Immuno-Blot (Western Blot)

The crude protein extracts are subjected to a Western blot, a technique well known to the person skilled in the art and described by H. Towbin et al., Proc. Ntl. Acad. Sci. U.S.A., 76, 1979, 4350–4354, which especially comprises the stages mentioned in Section 2.4)b).

The immunodetection of the protein of interest is carried out using an immune serum containing polyclonal antibodies recognizing the hybrid protein with chitinase activity (cf. WO92/01792 Example 5).

The antigen-antibody complex is then visualized with the aid of a streptavidin-biotin system conjugated to alkaline phosphatase using the Amersham RPN 23 kit ("Blotting detection kit"), used according to the instructions of the manufacturer.

The blot obtained shows, for the leaves of tobacco plants transformed by the plasmid pPH106, the presence of a protein of apparent molecular weight of approximately 26±6 kDa recognized by the polyclonal antibodies and absent from leaves of control tobacco plants. This protein has the same apparent molecular weight as the hybrid protein with chitinase activity described in the application WO92/01792.

c) Demonstration of the Chitinolytic Activity of the Recombinant Protein

The chitinolytic activity of the crude protein extracts of leaves of 5 tobacco plants transformed by the plasmid pPH106 (plants nos. 463, 464, 465, 468 and 469) and of crude protein extract of untransformed tobacco plant leaves (plant W38) is measured according to the following method:

The endochitinase activity of the protein is measured by a radiochemical method allowing the quantity of monomers or oligomers liberated by the enzyme from a substrate (tritiated chitin) to be estimated. This method, described by Molano et al., (1977, Anal. Biochem., 83, 648–656), is summarized below.

50 µl of a suspension of tritiated chitin of specific activity 0.58 MBq/ml is added to a volume of protein extract of 10 µl. The final volume is adjusted to 300 µl with 0.2 M sodium acetate buffer of pH5.0. After incubation at 30° C. for 90 min, the hydrolysis reaction of the chitin is stopped by 100 µl of 20% trichloroacetic acid. The reaction tubes are then centrifuged for 10 min at 12,000 g. An aliquot part of 100 µl of the supernatant containing the soluble oligomers of chitin is taken and the corresponding radioactivity is measured by liquid scintillation in the presence of 5 ml of scintillation mixture. The specific chitinolytic activity is expressed in dpm/µg of protein.

For the 5 plants selected on oxalic acid, the following values are obtained:

| Genotype | W 38 | 463 | 464 | 465 | 468 | 469 |
|---|---|---|---|---|---|---|
| Specific activity DPM/µg prot | 95 | 149 | 348 | 318 | 301 | 320 |

(W 38 = untransformed control tobacco)

It is confirmed in the table above that the extracts of tobacco plants transformed by the plasmid pPH106 have a chitinolytic activity which is significantly higher than that of the extract of control tobacco plants. Selection on oxalic acid thus allows plants expressing a gene of interest to be obtained on occurrence of the hybrid gene coding for a protein with chitinase activity described in the patent application WO92/01792.

---

---

What is claimed is:

1. A process for selecting plant cells comprising the steps of:
   transforming plant cells with a DNA sequence coding for an enzyme having oxalate oxidase activity and having a homology of at least 80% with SEQ ID No. 1, and
   selecting the plant cells which express said enzyme.

2. The process according to claim 1, wherein said enzyme with oxalate oxidase activity is an oxalate oxidase from cereals.

3. The process according to claim 2, wherein said enzyme having oxalate oxidase activity is the oxalate oxidase from wheat defined by sequence SEQ ID No. 1.

4. The process according to claim 2, wherein said enzyme having oxalate oxidase activity is the oxalate oxidase from barley.

5. A process according to claims 1, 2 or 3, wherein the DNA sequence coding for a protein coding an oxalate oxidase is the sequence SEQ ID No. 2.

6. The process according to claim 1, wherein the transformation of the plant cells is carried out with said DNA sequence in combination with a gene of interest.

7. Process according to claim 6, wherein the gene of interest codes for a protein which confers a resistance to pathogenic agents to plants.

8. Process according to claim 7, wherein the protein is a protein with endochitinase activity.

* * * * *